United States Patent [19]

Magers et al.

[11] 4,339,243

[45] Jul. 13, 1982

[54] STABILIZATION OF BENZIDINE-TYPE INDICATORS WITH VARIOUS ENHANCERS

[75] Inventors: Thomas A. Magers, South Bend; David L. Tabb, Elkhart, both of Ind.

[73] Assignee: Miles Laboratories, Inc., Elkhart, Ind.

[21] Appl. No.: 286,083

[22] Filed: Jul. 23, 1981

Related U.S. Application Data

[62] Division of Ser. No. 93,431, Nov. 13, 1979, Pat. No. 4,290,773.

[51] Int. Cl.³ ............................................. G01N 33/52
[52] U.S. Cl. .................................. 23/230 B; 23/932; 252/408; 422/56; 435/14; 435/28
[58] Field of Search ..................... 23/230 B, 901, 931, 23/932; 252/408; 422/56; 435/14, 28

[56] References Cited

U.S. PATENT DOCUMENTS

| | | | |
|---|---|---|---|
| 3,290,228 | 12/1966 | Gretton et al. | 422/56 X |
| 3,853,472 | 12/1974 | Rittersdorf et al. | 422/56 X |
| 3,917,452 | 11/1975 | Rittersdorf et al. | 422/56 X |
| 4,071,321 | 1/1978 | Lam | 422/56 |
| 4,089,747 | 5/1978 | Bruschi | 435/14 X |
| 4,148,611 | 4/1979 | Nand et al. | 23/230 B |
| 4,279,993 | 7/1981 | Magers et al. | 435/28 X |

Primary Examiner—Arnold Turk
Attorney, Agent, or Firm—Edward H. Gorman, Jr.

[57] ABSTRACT

An improved composition, device and method, whereby enhanced sensitivity is achieved in detecting test sample constituents such as glucose and blood. The improvement resides in the use of a broad range of compounds as enhancers for benzidine-type indicators. The enhancer tends to stabilize the blue colorform of such indicators.

5 Claims, No Drawings

STABILIZATION OF BENZIDINE-TYPE INDICATORS WITH VARIOUS ENHANCERS

This is a division of application Ser. No. 93,431, filed Nov. 13, 1979, now U.S. Pat. No. 4,290,773.

BACKGROUND OF THE INVENTION

1. Field of the Invention

The present invention relates to the field of analysis of a test sample for the presence of a constituent. More particularly, it relates to a composition capable of producing a detectable response in the presence of the constituent. Such a composition lends itself to the detection of various reducing sugars, hydrogen peroxide, peroxidase, peroxidatively active substances, hypochlorite and other analytes.

The analysis of test samples for the presence of sugars finds utility in many unrelated arts. Thus, the present invention pertains to such diverse arts as the brewing industry, biochemical research and medical diagnostics. In the brewing industry, for example, starch is converted to sugars, such as maltose, prior to actual fermentation. The presence of maltose is therefore carefully monitored to assure high yields from the grain starting material. Many biochemical systems require glucose in carefully controlled concentrations as their cellular energy source, and the research of such systems necessitates that these concentrations be carefully monitored. The medical profession utilizes sugar analysis to a great extent in diagnosing and controlling such diseases as diabetes mellitus, which manifests itself by abnormally high glucose concentrations in the blood and urine.

Likewise many analytical methods are presently available for detecting the presence of peroxidatively active substances in samples such as urine, fecal suspensions, and gastrointestinal contents. Hemoglobin and its derivatives are typical of such "peroxidatively active" substances because they behave in a manner similar to the behavior of the enzyme peroxidase. Such substances are also referred to herein as pseudoperoxidases. Peroxidatively active substances are enzyme-like in that they catalyze the redox reaction between peroxides and benzidine, o-tolidine, 3,3',5,5'-tetramethylbenzidine, 2,7-diaminofluorene or similar benzidine-type indicator substances, thereby producing a detectable response such as a color change. Most methods for determining the presence of occult blood in test samples rely on this pseudoperoxidase activity.

Thus, the field of the present invention extends to a very diverse assortment of pursuits. It finds applicability wherever sugar analysis becomes a matter of significance, be it in brewing, the food industry, scientific research or medicine. Moreover, it lends itself to a variety of techniques for determining the presence of a peroxidase or pseudoperoxidase. In fact, the present invention finds utility in any field where its unique propensity to exhibit a detectable response is adaptable. Any system which can ultimately provide $H_2O_2$ as a reaction product or which contains peroxidase or a pseudoperoxidase is suitable for application of the present invention, as are other systems such as swimming pool water containing hypochlorite and other strongly oxidizing systems.

2. Description of the Prior Art

The history of sugar analysis is perhaps most noteworthy because it has seen dramatic change over the years, both in the basic chemistries utilized and in its format. For the most part these analyses can be characterized as oxidizing systems which, when reduced, initiate reaction conditions leading to a detectable response, such as a color change or change in wavelength of ultraviolet light absorbed or reflected by the system. Thus, reducing sugars will convert silver oxide to metallic silver, and, if a solution of the sugar is applied to a piece of filter paper impregnated with silver oxide, a black dot develops. F. Feigl, *Chem. Ind.*, Vol. 57, p. 1161, London (1938). Similarly, o-dinitrobenzene and the 3,4- and 3,5-isomers of dinitrophthalic acid give a sensitive color reaction (forming violet shades) when heated with reducing sugars in $Na_2CO_3$. T. Momose, et al., *Chem. Pharm. Bull. Tokyo*, Vol. 12, p. 14 (1964); F. Feigl, *Spot Tests in Organic Analysis*, 7th Edition, pp. 338–339, Elsevier Publ. Co., New York (1966).

But as early as 1849 it was known that reducing sugars would cause an alkaline solution of $CuSO_4$ to precipitate the yellow to red Copper(I)oxide (oxyhydrate). H. Fehling, *Ann.*, Vol. 72 (1849). See also B. Herstein, *J. Am. Chem. Soc.*, Vol. 32, p. 779 (1910). This early milestone, known as the Fehling test, lent impetus to the development of a far more sensitive test which utilized silver oxide in ammonia, the so-called Tollens reagent, which reacts readily with reducing agents to produce a black precipitate of metallic silver, often forming a mirror on the inside walls of glass reaction vessels. B. Tollens, *Ber.*, Vol. 14, p. 1950 (1881); Vol. 15, p. 1635, 1828 (1882).

Because of the relatively high incidence of diabetes mellitus and its accompanying serious clinical consequences, high interest from the biological and medical professions arose in new techniques for analyzing glucose levels in urine and serum. This keen interest led to the development of several procedures which deviate dramatically from their solution chemistry forbers. These utilize sophisticated biochemical systems which can be incorporated into dry, dip-and-read devices, used in solution or suspension techniques, or in conjunction with spectrophotometers and other hardware.

Of these new techniques, the present invention leads itself especially well to an enzymatic system wherein the analyte, for instance glucose, is a substrate for a particular enzyme, the reaction products being capable of eliciting a detectable response from a family of indicator compounds known loosely in the art as "benzidine-type indicators". These will be more carefully defined, infra, but for the present suffice it to say these compounds can undergo color changes in the presence of hydrogen peroxide and the enzyme peroxidase. The glucose/glucose oxidase system exemplifies the prior art, wherein glucose is oxidized to gluconic acid with the concomitant formation of $H_2O_2$ in accordance with:

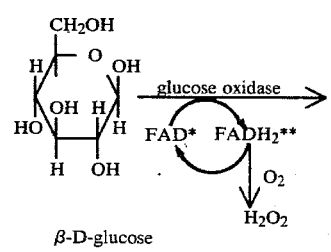

β-D-glucose

-continued

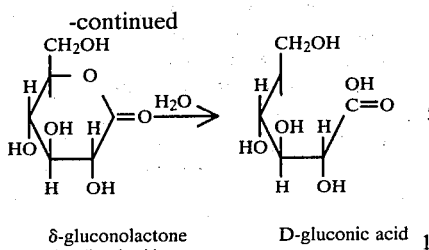

δ-gluconolactone     D-gluconic acid

*The coenzyme-flavenine adenine dinucleotide
**Same, reduced form

It is the concomitant formation of hydrogen peroxide which facilitates the subsequent, indicator-related steps leading to observable color formation or other detectable response. Thus a benzidine-type indicator responds in the presence of hydrogen peroxide and peroxidase by changing its light absorptive capability.

In practice, this technology is presently utilized for glucose analysis in the form of dip-and-read reagent strips such as those marketed by the Ames Division of Miles Laboratories, Inc. under the trademark CLINISTIX® and others. Broadly, these comprise a plastic strip, at one end of which is mounted an absorbent paper portion impregnated with the appropriate enzymes, indicator compound and buffering agents as the principal active ingredients. They are used by dipping the reagent-bearing end into the test sample, removing it and comparing any color formed in the paper with a standard color chart calibrated to various glucose concentrations.

Several patents have issued which are deemed pertinent to the present invention with respect to its application to glucose analysis. U.S. Pat. No. 2,848,308, issued to Alfred H. Free, disclosed and claimed the basic enzyme chemistry whereby glucose oxidase, peroxidase and a benzidine-type indicator are used in a reagent strip to determine glucose in urine or other bodily fluid. U.S. Pat. No. 3,753,863, issued to Speck discloses the use of lower alkane polyols to "stabilize" indicator solutions of the benzidine type. Finally, U.S. Pat. No. 4,071,317, issued to Lam, discloses the stabilization of an occult blood-sensitive composition through the use of certain sulfone, sulfoxide and amide compounds as diluents during preparation of the composition. This latter composition comprises an organic hydroperoxide compound, and an indicator compound such as of the benzidine type.

As in the case of sugar analysis, several methods for peroxidase or pseudoperoxidase analysis have evolved over the years which rely on enzyme-like catalysis of the oxidation of color-forming indicators in the presence of hydrogen peroxide. Primarily these include wet chemical procedures and "dip-and-read" type reagent-bearing strips. Of the former, a typical example is set forth in Richard M. Henry, et al., *Clinical Chemistry Principles and Techniques*, Hagerstown, Maryland: Harper and Row (1974), pp. 1124–1125. This procedure involves the use of glacial acetic acid (buffer), diphenylamine (indicator), and hydrogen peroxide. While such wet methods have proven analytical ability, they are nevertheless fraught with obvious shortcomings, not the least of which are poor reagent stability and inadequate sensitivity. Inherent to such reagent solutions is a decline in stability (ergo sensitivity) so rapid that fresh reagent solutions must be prepared after several days of storage, a necessity resulting in both excessive time required of analytical personnel, and poor economy because of having to waste costly reagents.

A second method for the determination of peroxidatively active substances, and the one presently preferred by most clinical assayists and analysts, utilizes "dip-and-read" reagent strips. Typical of such devices are reagent strips manufactured by the Ames Division of Miles Laboratories, Inc. and sold under the name HEMASTIX®. These comprise, in essence, a porous paper matrix affixed to a plastic strip or handle. The matrix is impregnated with a buffered mixture of an organic hydroperoxide and o-tolidine. Upon immersion in a liquid containing hemoglobin, myoglobin, erythrocytes or other pseudoperoxidases, a blue color develops in the matrix, the intensity of which is proportional to the concentration of the peroxidatively active substance in the sample. Thus, by comparing the color developed in the matrix to a standard color chart, the assayist can determine, on a semi-quantitative basis, the amount of unknown present in the sample.

The advantages of reagent strips over wet chemistry methods are predominantly twofold: strips are easier to use because neither the preparation of reagents nor the attendant apparatus is required; and greater stability of reagents is afforded, resulting in greater accuracy, sensitivity and economy.

But the inherent advantages of strips over wet chemistry notwithstanding, the characteristics of stability and sensitivity are in need of still further improvement. Whereas these properties in current state-of-the-art strips for determining pseudoperoxidases, sugars and other analytes are greatly preferred over those of wet chemical methods, there would nevertheless accrue a great advance in the art if such strips could be made even more stable during storage and even more sensitive to their respective analytes.

At least three attempts at improving pseudoperoxidase-sensitive systems are recorded in the prior art. A recitation in *Chemical Abstracts* Volume 85, page 186 (1976) describes a two-dip method for preparing occult blood-sensitive reagent strips containing o-tolidine and phenylisopropyl hydroperoxide. In this method, a solution was made of the indicator (o-tolidine.2HCl) and polyvinylpyrrolidone in ethanol. To this solution was added a small amount of surfactant and enough citrate buffer to provide a pH of 3.7. Filter paper strips impregnated with ethyl cellulose were dipped in this solution and dried. The thus-impregnated filter paper was subsequently dipped into a second solution containing 1,4-diazabicyclo[2.2.2]octane, phenylisopropyl hydroperoxide and polyvinylpyrrolidone dissolved in an ethanol-toluene mixture. The thrust of this experiment was to stabilize the peroxide and indicator combination through the use of the bicyclo-octane derivative and the polyvinylpyrrolidone.

A second such method is disclosed in U.S. Pat. No. 3,853,471. This patent teaches the use of phosphoric or phosphonic acid amides where the substituent amido groups are primarily N-morpholine radicals.

Besides these attempts, there also exists the disclosure of U.S. Pat. No. 3,252,762 wherein the organic hydroperoxide is physically encapsulated within a colloidal material such as gelatin. When such a test strip is utilized, the aqueous test sample dissolves the gelatin capsules, thereby freeing the hydroperoxide for further reaction with the indicator in the presence of a peroxidatively active substance.

Each of these prior attempts was aimed at stabilizing the reagents so that the potentially incompatible reactive ingredients (hydroperoxide and indicator) would not prematurely combine and thereby render the test strips less sensitive. Hence, it can be said that the prior art methods were not directed towards the combined objectives of simultaneously enhancing stability and sensitivity, but rather they attempted to preserve existing sensitivity by preventing reagent decomposition during storage.

Another prior art reference which is of interest to one considering the general concepts discussed herein is U.S. Pat. No. 3,236,850. This patent is directed towards stabilizing organic hydroperoxides used as catalysts and oxidizing agents. The patentees in this reference disclose the use of primary, secondary, or tertiary amine salts with organic peroxides. This reference is in no way directed toward reagent test strips, or other analytical techniques.

To summarize the state of the art prior to the present invention, sugar-sensitive chemistries began to appear on the analytical scene as early as the middle of the 19th century with the advent of Fehling's solution and Tollens' reagent. Most of the "purely chemical" systems which have since emerged have been largely superseded by biochemical systems, particularly those which comprise a sugar oxidase, peroxidase and a peroxide-sensitive indicator of the benzidine type. These latter indicator compounds have been said to be stabilized by the presence of lower alkyl polyols.

Pseudoperoxidase-sensitive chemistries were also utilized early on as wet chemistry techniques, having given way to dip-and-read techniques involving an organic peroxide and an indicator, such as a benzidine derivative, impregnated in a carrier matrix. Attempts at stabilizing these reagents have included (a) the concomitant use of bicyclooctane and polyvinylpyrrolidone, (b) phosphoric or phosphonic acid amides, (c) physical separation of reagents using gelatin capsules, and (d) primary, secondary and tertiary amine salts.

Finally, a composition sensitive to the presence of occult blood in urine is taught to be stabilized if formulated in the presence of certain sulfone, sulfoxide and/or amide compounds. There is no teaching to applicants' knowledge, anywhere in the prior art suggesting the presently disclosed and claimed composition and test device, or method for their use.

SUMMARY OF THE INVENTION

Briefly stated, the present invention relates to an improved composition, test device and method for detecting the presence of a constituent in a test sample. The composition is capable of producing a detectable response, such as a color change, in the presence of the constituent; and comprises a benzidine-type indicator and an enhancer compound having the structure

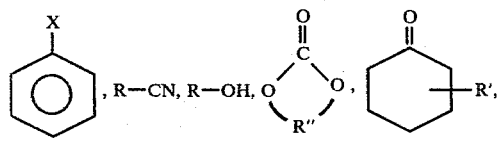

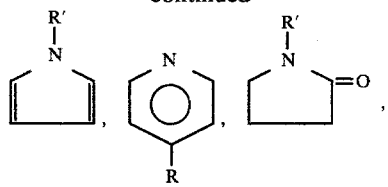

or mixtures thereof, wherein R is lower alkyl, R' is H or lower alkyl, R" is lower alkylene, and X is OH, CN, $NO_2$, CHO, $SO_3R'$ or NRCOR', and wherein R—OH is a monoalkanol.

The present invention also includes a test device comprising a carrier matrix incorporated with the composition. The presence of the particular constituent is determined by contacting the test sample with the device or composition, and observing any detectable response.

DETAILED DESCRIPTION OF THE INVENTION

The present invention is a ramification of the well-known "benzidine-type" indicator system. Benzidine and its derivatives have long been used as chromogenic indicators in assays for such diverse test sample constituents as hypochlorite ion in swimming pool water, and glucose or occult blood in urine. Their ability to develop easily recognizable blue hues of varying intensities renders them capable of both qualitative and semi-quantitative utility. Since the present invention pertains to this indicator system on a broad scale, it is deemed important to elucidate the types of compounds included within the scope of the term "benzidine-type" indicator, as well as many currently known systems with which such indicators have been found to be efficacious.

Benzidine and its derivatives ("benzidine-type" indicators) are best defined in terms of the structure

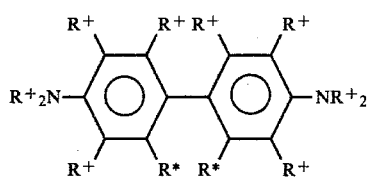

in which the $R^+$ and $R^*$ substituents, same or different, can be hydrogen, lower alkyl (i.e., alkyl having 1 to about 6 carbon atoms), lower alkyloxy (i.e., alkyloxy having 1 to about 6 carbon atoms), aryl or aryloxy. Moreover, the $R^*$ substituents can together form $-(CH_2)_n$ in which n is 1 or 2. In addition to the above characterizations of $R^+$ and $R^*$, it is understood that these groups, themselves, can be substituted such as with hydroxy, halogen, cyano, etc. Typical compounds embraced by the term "benzidine-type" indicator include benzidine, o-tolidine, o-dianisidine, 3,3',5,5'-tetramethylbenzidine (hereafter "tetramethylbenzidine"), 3,3',5,5'-tetra(alkyl)benzidine, the various N- and N'-substituted benzidines and others.

Although the mechanism of color formation from benzidine-type and other indicators in the presence of certain analytes is not known to a certainty, it is known that two sequentially occurring colorforms result: a first species which is blue in color, and a second which is brown. Because the blue species tends to be transient, ultimately metamorphosing to the brown, it is necessary to look for the color change within a prescribed time period. Otherwise the true significance of color change is lost, as subtle shades of blue—which are easily distinguishable—give way to the less easily interpreted brown hues. The higher the analyte concentration in the test sample, the more aggravated this problem becomes, due to the limiting effect on capacity to detect the higher ranges of analyte concentrations. Thus, it can be seen that it is highly advantageous to extend the duration of the blue species, thereby permitting greater differentiation between concentrations, as well as providing higher and lower limits to the detectable concentration ranges.

Moreover, because analytical tools such as reagent strips are not used immediately after manufacture, but are usually stored for relatively long periods, and because too long a period between manufacture and use can result in a loss in efficacy leading to false negative results, enhanced shelf life can be a marked asset: the better the shelf life, the more dependable the analytical results.

In addition to the benzidine-type indicator itself, the invention contemplates a myriad of reagent systems which, in the presence of a particular analyte, promote the detectable indicator response, such as a color appearance or change. Thus, if the present composition were to be employed for hypochlorite determination, the indicator and enhancer composition could be employed by themselves, no further reagents being necessary except, perhaps, a buffer.

For the determination of glucose in urine, on the other hand, a reagent system is employed comprising, in addition to the present composition, glucose oxidase, peroxidase and a suitable buffer. When such a system is contacted with a urine sample containing glucose, the glucose oxidase catalyzes the oxidation of glucose, yielding $H_2O_2$ as a by-product. In the presence of peroxidase, the $H_2O_2$ causes a color change or appearance in the benzidine-type indicator/enhancer composition. The purpose of the buffer, if included, is to optimize these reactions by providing the most advantageous pH.

The determination of occult blood or other pseudoperoxidase, or of peroxidase, requires still another reagent system in addition to the present composition: an organic hydroperoxide, such as cumene hydroperoxide, and, preferably, a suitable buffer. Thus, if pseudoperoxidase is present in the test sample, the organic peroxide/pseudoperoxidase system will interact with the composition of the present invention to yield a color change enabling qualitative and semi-quantitative pseudoperoxidase analysis.

The enhancer compound of the present invention has been found to promote sensitivity by permitting an observable color appearance at analyte levels lower than those possible with identical systems without the enhancer present. Similarly, the enhancer also permits analyte to be semi-quantitatively assessed at much higher concentrations. Thus, the entire range of analyte concentrations detectable with a particular reagent system and benzidine-type indicator may be expanded when the enhancer of the present invention is present in the formulation.

The compounds which are within the meaning of the term "enhancer compound" as used herein are indeed numerous. Moreover, these compounds take on a myriad of seemingly unrelated types, including such chemically diverse compounds as phenol, acetonitrile, nitrobenzene, benzonitrile, ethylene carbonate, cyclohexanone, N-methylpyrrolidone, 4-picoline and pyrrole. Broadly, these compounds fall into the following generic categories:

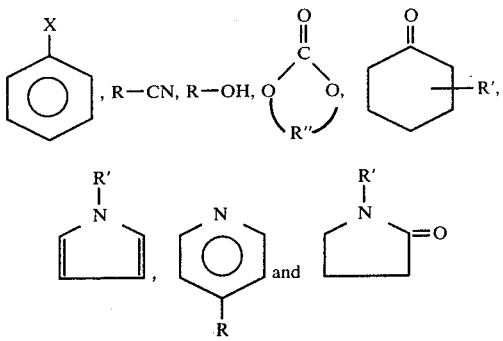

wherein X is OH, CN, $NO_2$, CHO, $SO_3R'$ or $NRCOR'$, R is lower alkyl, R' is H or lower alkyl, R" is lower alkylene, and R—OH is a monoalkanol. By "lower alkyl" is meant a hydrocarbon radical having from 1 to about 6 carbon atoms, including methyl, ethyl, n-propyl, isopropyl, n-butyl, isobutyl, tert-butyl, cyclobutyl, and all the various normal, branched and cyclic isomers of pentyl and hexyl. Moreover, R and R' can be substituted, such as with hydroxyl, halogen, cyano or other substituents. By "lower alkylene" is meant a divalent aliphatic radical having 1 to about 6 carbon atoms, including $-CH_2-$, $-CH_2CH_2-$, and $-CH_2CH_2CH_2-$.

The amount of enhancer used in conjunction with the benzidine-type indicator is not critical, although an amount in the range of about 50 to 800 or more mole percent based on the moles of indicator has been found to be effective in achieving the aforementioned enhanced indicator sensitivity. Using this basis as a guideline, although not necessarily a requisite, the amounts of the present composition to be used with the various chemistries for the desired analytes can be easily determined from the prior art, as well as from the Examples provided below. Moreover, given the present teachings, it would be a routine laboratory exercise to determine optimum amounts.

The test device of the present invention comprises a carrier matrix incorporated with the indicator/enhancer composition. Moreover, it can be additionally incorporated with any art-recognized or other reagent system useable with a benzidine-type indicator, such as the glucose- and pseudoperoxidase-sensitive systems discussed above.

The carrier matrix utilized in forming the test device can take on a multitude of forms. Thus, U.S. Pat. No. 3,846,247 teaches the use of felt, porous ceramic strips, and woven or matted glass fibers. Additionally, U.S. Pat. No. 3,552,928 teaches the use of wood sticks, cloth, sponge material, and argillaceous substances. The use of synthetic resin fleeces and glass fiber felts as a carrier matrix is suggested in British Pat. No. 1,369,139. Another British Pat. No. 1,349,623, proposes the use of light-permeable meshwork of thin filaments as a cover for an underlying paper matrix. Polyamide fibers are taught in French Pat. No. 2,170,397. These suggestions notwithstanding, however, the material predominantly used in the art as a carrier matrix, and that which is especially suitable for the present invention, is a bibulous paper such as filter paper. It can thus be seen that there is a great deal of leeway in selecting an appropriate material for use as a carrier matrix, and the matrix can take on various physical forms. All of these types are intended as being within the scope of the present invention.

Whichever is chosen, a web of carrier matrix material can be incorporated with the present composition in several ways. The web can be drawn through a solution or suspension of the indicator and enhancer in an appropriate solvent such as water, methanol, benzene, cyclohexane, etc. After drying, the composition-laden matrix web can then be slit into strips about 0.5 cm. wide and fastened to one edge of a strip of plastic backing material measuring about 8 cm. in width. This can be achieved using a double-faced adhesive tape known as Double Stick available from the 3M Company. The backing material with the matrix strip in place is then cut widthwise to form reagent strips measuring 8×0.5 cm. having a 0.5 cm. square of reagent-laden carrier matrix at one end, the other end serving as a handle.

Another way of incorporating a carrier matrix with the present composition is by printing. U.S. Pat. No. 4,046,513 describes such a technique whereby an ink comprising the composition is silk screened onto a plastic carrier matrix. Still other ways, such as spraying the composition onto the matrix, are part of the prior art, and thus would be within the ken of a person of ordinary skill in the art.

The following Examples are provided to further illustrate the composition and test device of the present invention, as well as the method for their use. Included are the embodiments of the invention presently considered preferred, and which are presently deemed to be the best mode of performance of the invention. Moreover, as can be seen from the foregoing discussion, the presently disclosed concepts are very broad in scope; and the succeeding Examples should not be deemed as being in any way limiting.

EXAMPLES I-XI

The Effects of Various Enhancers on o-Tolidine

Because o-tolidine is a benzidine-type indicator presently widely employed in commercial reagents for detecting glucose, occult blood, hypochlorous acid (hypochlorite), and other analytes, an experiment was conducted to evaluate the effects of various enhancers of the present invention on the performance of that indicator. Specifically, a reagent composition comprising the indicator and one of various enhancers was contacted with sodium hypochlorite solutions of increasingly higher concentrations. The appearance of blue color, indicative of the presence of hypochlorite, was observed as the amount of hypochlorite was increased, until the advent of brown color was observed. The amount of hypochlorite required to induce the brown chromogen to the extent where blue was not observable was then recorded as a function of the various enhancers and a control system without any enhancer present.

A stock solution was prepared from the following ingredients, which were added in the order as listed.

Distilled water: 184.0 milliliters (ml)
o-Tolidine.2HCl: 2.0 grams (g)
Acetone: 116.0 ml
Citrate buffer (pH 5)*: 94.0 ml

*Prepared from 208 ml distilled water, 15.4 g citric acid (anhydrous) and 68 g Na3 citrate.2H2O.

Eleven 19.7 ml aliquots of this stock solution were set aside. To ten of these was added 0.1 g of one of the enhancers listed in Table I.

Each aliquot thus prepared was used to impregnate a piece of Eaton & Dikeman 204 filter paper measuring 3.5 by 7 inches. The stock solution without enhancer was used to impregnate another piece of filter paper for use as a control. The impregnated papers were dried in a forced air oven at about 50° C. for about 10 minutes. Each dried paper was attached to one side of a similar-sized sheet of double-faced adhesive tape (3M Company, Double Stick Y-915). The resultant laminates were slit to measure 0.20×7 inches, and the remaining protective paper removal from the adhesive tape, whereupon the laminates were affixed along the wider edge of polystyrene sheets measuring 3.25×7 inches. The polystyrene/adhesive/impregnated paper composites were then slit perpendicular to their wider edge to provide plastic strip devices each measuring 0.2×3.25 inches, having an impregnated paper portion measuring 0.2 inches square at one end, the other end serving as a handle.

Each of the eleven sets of enhancer-containing devices, plus the control set, was studied by brief immersion (1–2 seconds) of a device in a hypochlorite solution of known concentration. The hypochlorite solutions (55 in all) were prepared in graduated concentrations ranging from 0.05 gram/100 ml water (g%) to 2.75 g%, each succeeding solution being 0.05 g% more concentrated than its predecessor. Strips of a particular set were dipped in each of these solutions, and the appearance of color was observed after about 60 seconds. The highest concentration of hypochlorite wherein blue color could be observed in a device after 60 seconds was recorded. The data for the control and each enhancer tested is recorded in Table I.

TABLE I

| Example No. | Enhancer | NaClO (g%)* |
|---|---|---|
| I | Control | 0.70 |
| II | Phenol | 0.85 |
| III | Nitrobenzene | 2.40 |
| IV | Benzonitrile | 2.20 |
| V | Acetonitrile | 1.40 |
| VI | n-Hexanol | 0.90 |
| VII | Ethylene carbonate | 2.45 |
| VIII | Cyclohexanone | 1.35 |
| IX | Pyrrole | 0.95 |
| X | 4-Picoline | 1.10 |
| XI | N-Methyl-2-pyrrolidone | 2.15 |

*Highest concentration wherein blue color was still observable 60 seconds after dipping.

EXAMPLES XII-XXII

The Effects of Various Enhancers on 3,3',5,5'-Tetramethylbenzidine (TMB)

Experiments were conducted to assess the effects of the enhancers of the present invention on TMB.

The procedure followed was identical to that of Examples I-XI except that 3.0 g TMB was substituted for o-tolidine in formulating the stock solution. The results are tabulated in Table II.

TABLE II

| Example No. | Enhancer | NaClO (g%)* |
|---|---|---|
| XII | Control | 0.65 |
| XIII | Phenol | 0.80 |
| XIV | Nitrobenzene | 2.50 |
| XV | Benzonitrile | 2.40 |

TABLE II-continued

| Example No. | Enhancer | NaClO (g%)* |
|---|---|---|
| XVI | Acetonitrile | 1.50 |
| XVII | n-Hexanol | 0.90 |
| XVIII | Ethylene carbonate | 2.60 |
| XIX | Cyclohexanone | 1.40 |
| XX | Pyrrole | 1.05 |
| XXI | 4-Picoline | 1.30 |
| XXII | N-Methyl-2-pyrrolidone | 2.25 |

*Highest concentration wherein blue color was still observable 60 seconds after dipping.

The results of the experiments described in the Examples demonstrate conclusively the unexpected stabilization of the blue colorform of both o-tolidine and 3,3',5,5'-tetramethylbenzidine. With each of these indicators, strong blue responses to increasing concentrations of hypochlorite were in evidence in the presence of an enhancer of the present invention, whereas the controls (Examples I and XII) without an enhancer soon lost their blue hues, giving way to the secondary brown hues. In each case the presence of an enhancer yielded a more stable blue than did the controls.

What is claimed is:

1. In a composition for detecting the presence of a constituent in a test sample, said composition comprising a benzidine-type indicator, the improvement wherein said composition additionally comprises an enhancer compound having the structure

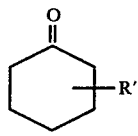

wherein R' is H or lower alkyl.

2. The composition of claim 1 wherein said enhancer is cyclohexanone.

3. A test device for determining the presence of a constituent in a test sample, said device comprising a carrier matrix incorporated with the composition of claim 1 or 2.

4. A method for determining the presence of a constituent in a test sample, said method comprising contacting said test sample with the composition of claim 1 or 2 and observing a detectable response.

5. A method for determining the presence of a constituent in a test sample, said method comprising contacting said test sample with the device of claim 3, and observing a detectable response.

* * * * *